(12) United States Patent
Hauptmann et al.

(10) Patent No.: US 10,758,165 B2
(45) Date of Patent: Sep. 1, 2020

(54) ADAPTIVE STIMULATION TONE ADJUSTMENT FOR TREATING TINNITUS IN ACOUSTIC COORDINATED RESET MEUROMODULATION SYSTEMS, DEVICES, COMPONENTS AND METHODS

(71) Applicant: Aureliym GmbH, Bad Neuenahr-Ahrweiler (DE)

(72) Inventors: Christian Hauptmann, Starnberg (DE); Mark Williams, London (GB); Markus Haller, Beirut (LB)

(73) Assignee: Aureliym GmbH, Bad Neuenahr-Ahrweiler (DE)

( * ) Notice: Subject to any disclaimer, the term of this patent is extended or adjusted under 35 U.S.C. 154(b) by 0 days.

(21) Appl. No.: 16/323,256

(22) PCT Filed: Aug. 8, 2017

(86) PCT No.: PCT/EP2017/000960
§ 371 (c)(1),
(2) Date: Feb. 4, 2019

(87) PCT Pub. No.: WO2018/028828
PCT Pub. Date: Feb. 15, 2018

(65) Prior Publication Data
US 2019/0183391 A1 Jun. 20, 2019

Related U.S. Application Data

(60) Provisional application No. 62/372,006, filed on Aug. 8, 2016.

(51) Int. Cl.
*A61B 5/12* (2006.01)
*A61B 5/00* (2006.01)
*H04R 25/00* (2006.01)

(52) U.S. Cl.
CPC .............. *A61B 5/128* (2013.01); *A61B 5/721* (2013.01); *A61B 5/7267* (2013.01); *H04R 25/75* (2013.01);
(Continued)

(58) Field of Classification Search
CPC ........... H04R 25/75; A61B 5/12; A61B 5/128; A61B 5/721; A61B 5/7267; A61B 5/74;
(Continued)

(56) References Cited

U.S. PATENT DOCUMENTS 5,403,262 A * 4/1995 Gooch ..................... A61B 5/12
600/28
5,795,287 A * 8/1998 Ball ..................... H04R 25/502
600/25

(Continued)

FOREIGN PATENT DOCUMENTS

EP 2842530 A1 3/2015

OTHER PUBLICATIONS

International Search Report and Written Opinion issued in International Application No. PCT/EP2017/000960 dated Nov. 8, 2017.
(Continued)

*Primary Examiner* — Jason R Kurr
(74) *Attorney, Agent, or Firm* — Quinn IP Law

(57) ABSTRACT

Described and disclosed herein are various embodiments of systems, devices, components and methods configured to employ acoustic coordinated reset neuromodulation therapies that are capable of adjusting or modulating at least one of the intensity, auditory filter bandwidth, and center frequency of therapeutic stimulation signals delivered to an individual patient, where in one embodiment such signals are tuned to have intensities that are above or slightly above the individual patient's hearing threshold.

19 Claims, 8 Drawing Sheets

(52) U.S. Cl.
CPC ......... *A61B 5/74* (2013.01); *A61B 2560/0223* (2013.01); *A61B 2562/0204* (2013.01)

(58) Field of Classification Search
CPC ..... A61B 2560/0223; A61B 2562/0204; A61F 11/00; A61F 11/045; A61N 1/361; A61N 1/36171; A61N 1/36036; A61N 1/36038
See application file for complete search history.

(56) References Cited

U.S. PATENT DOCUMENTS

| | | | |
|---|---|---|---|
| 6,155,971 A * | 12/2000 | Calhoun | A61B 5/121 600/28 |
| 7,520,851 B2 * | 4/2009 | Davis | A61B 5/121 600/25 |
| 8,608,638 B2 * | 12/2013 | McGuire | A61M 21/00 600/25 |
| 9,549,269 B2 * | 1/2017 | Notzel | A61B 5/128 |
| 2013/0163797 A1 | 6/2013 | Suzman et al. | |
| 2015/0051655 A1 * | 2/2015 | Kilgard | A61N 1/36036 607/3 |

OTHER PUBLICATIONS

Christian Hauptmann et al., "Acoustic Coordinated Reset Neuromodulation in a Real Life Patient Population with Chronic Tonal Tinnitus", Biomed Research International, vol. 2015, Jan. 1, 2015, pp. 1-8.

* cited by examiner

ADAPTIVE STIMULATION TONE ADJUSTMENT FOR TREATING TINNITUS IN ACOUSTIC COORDINATED RESET NEUROMODULATION SYSTEMS, DEVICES, COMPONENTS AND METHODS

FIELD OF THE INVENTION

Various embodiments of the systems, devices, components and methods disclosed and described herein relate to acoustic coordinated reset neuromodulation therapies delivered to patients via external and/or implanted systems, devices and components.

BACKGROUND

Acoustic coordinated reset (CR) neuromodulation therapy is a form of noninvasive neuromodulation therapy for treating primary tinnitus, in particular, the frequency-specific, often tonal tinnitus commonly seen in these patients. See, for example, "Counteracting tinnitus by acoustic coordinated reset neuromodulation," Restor. Neurol. Neurosci. 30(2): 137-159. Tass et al., 2012.

Acoustic CR neuromodulation uses acoustic signals that stimulate the auditory neural tracts as they account for hearing level and psychoacoustic characteristics of the tinnitus percept (Tass et al., 2012). These techniques employ well-accepted neuroplasticity principles and were developed using computational modeling. See, for example, "A model of desynchronizing deep brain stimulation with a demand-controlled coordinated reset of neural subpopulations," Biol Cybern 89(2):81-88, Tass, 2003. See also "Long-term anti-kindling effects of desynchronizing brain stimulation: a theoretical study," Biol. Cybern 94(1):58-66, Tass, P. A., Majtanik M., and "Unlearning tinnitus-related cerebral synchrony with acoustic coordinated reset stimulation: theoretical concept and modelling," Biol. Cybern. 106(1):27-36, Tass and Popovych, 2012.

Using the systematic tonotopic organization of the peripheral and central auditory system in the auditory cortex in the temporal lobe, acoustic tones, typically four different frequencies centered around the characteristic frequency of the patient's tinnitus percept, are determined and delivered in non-simultaneous sequences several hours per day for several weeks (lass et al., 2012). The four tones are designed to activate different areas of the central auditory system in a coordinated manner.

Despite their relative sophistication, many known acoustic CR techniques neuromodulation techniques do not provide or deliver stimulation signals that have intensities appropriately or optimally matched to the individual hearing thresholds of hearing impaired patients. What is needed are ways to deliver audio signals to hearing impaired patients where the signals have intensities that are optimally matched to individual hearing thresholds.

SUMMARY

In one aspect, the invention provides a method of providing stimulation signals for acoustic coordinated reset neuromodulation therapy to be delivered to a patient. The method comprises providing an audio-detection threshold calibration (such as an audiogram), which defines a frequency dependent hearing level of the patient. The method further comprises providing a frequency-discrimination threshold calibration, which defines an intensity dependent bandwidth of frequencies not discriminable by the patient. The frequency-discrimination threshold calibration represents an implementation of an auditory filter bandwidth as will be described in more detail later on. Moreover, the method comprises evaluating a tinnitus frequency for tinnitus experienced by a patient determining a tinnitus bandwidth as the width of a tinnitus frequency band centered at the tinnitus frequency; and generating at least one (first) primary stimulation signal with a (first) primary stimulation frequency and a (first) primary stimulation intensity such that the (first) primary stimulation intensity exceeds a hearing level of the patient, as defined by the audio-detection threshold calibration at the (first) primary stimulation frequency, by a predetermined quantity; and the (first) primary stimulation frequency is offset from the tinnitus frequency such that a (first) primary stimulation frequency band and the tinnitus frequency band overlap by a predetermined amount, wherein the (first) primary stimulation frequency band represents a frequency band centered at the (first) primary stimulation frequency and having a (first) primary stimulation bandwidth according to a bandwidth defined by the frequency-discrimination threshold calibration at the (first) primary stimulation intensity.

Preferably, generating the at least one primary stimulation signal comprises:

determining at least one initial primary stimulation frequency offset from the tinnitus frequency;

determining the primary stimulation intensity based on the at least one initial primary stimulation frequency according to the audio-detection threshold calibration;

determining the (first) primary stimulation bandwidth as a bandwidth defined by the frequency-discrimination threshold calibration at the (first) primary stimulation intensity;

modifying the at least one primary stimulation frequency so that the tinnitus frequency band and a modified primary stimulation frequency band overlap by the predetermined amount, wherein the modified primary stimulation frequency band represents a frequency band with the determined primary stimulation bandwidth centered at the modified (first) primary stimulation frequency; and generating the at least one primary stimulation signal based on the modified primary stimulation frequency and the primary stimulation intensity.

Preferably, in an iterative implementation, the method may further comprise:

modifying the at least one primary stimulation intensity based on the modified at least one primary stimulation frequency such that the modified primary stimulation intensity exceeds a hearing level of the patient, as defined by the audio-detection threshold calibration at the modified primary stimulation frequency, by a predetermined quantity;

modifying the at least one primary stimulation bandwidth on the basis modified at least one primary stimulation intensity, which can be done as in the initial step of determining the primary stimulation bandwidth; and adjusting the at least one primary stimulation frequency so that the tinnitus frequency band and an adjusted primary stimulation frequency band overlap by the predetermined amount, wherein the adjusted primary stimulation frequency band represents a frequency band with the modified primary stimulation bandwidth centered at the adjusted primary stimulation frequency Preferably, there is provided a method of delivering stimulation signals for acoustic coordinated reset neuromodulation therapy to a patient's auditory cortex, comprising evaluating a tinnitus frequency for tinnitus experienced by the patient; determining a tinnitus bandwidth as the width of a tinnitus frequency band centered at the tinnitus frequency; determining at least one primary stimulation frequency offset from the tinnitus frequency; determining at least one primary stimulation intensity based on the at least one primary stimulation frequency according to an audio-detection threshold calibration; determining at least one primary stimulation bandwidth as the width of at least one primary stimulation frequency band centered at the at least one primary stimulation frequency on the basis of the at least one primary stimulation intensity; modifying the at least one primary stimulation frequency on the basis of the tinnitus frequency, the tinnitus bandwidth and the at least one primary stimulation bandwidth so that the tinnitus frequency band and the at least one primary stimulation frequency band overlap by a predetermined amount; generating at least one primary stimulation signal based on the modified at least one primary stimulation frequency and the at least one primary stimulation intensity; and optionally delivering to the patient the at least one primary stimulation signal to treat the patient's tinnitus.

In other words, in one aspect there is provided a method of providing, particularly generating, stimulation signals for acoustic coordinated reset neuromodulation therapy. The method comprises evaluating a tinnitus frequency.

Evaluation of the tinnitus frequency of the patient can be carried out by various pitch matching methods to determine a tinnitus frequency (also called pitch) as experienced by the patient. For example, a tunable tone is delivered to the patient, while the patient adapts the frequency of the tunable tone until it matches the tinnitus frequency as experienced by the patient. Depending on the type of the tinnitus, the frequency of the tinnitus as experienced by the patient may be a center frequency of a noise or it may be a fundamental frequency of a harmonic tone.

The method further comprises determining, or calculating, a tinnitus bandwidth. Based on the structure and functioning of the human auditory system, it is possible to model the size and location of areas activated in the cortex by auditory stimuli by means of frequency bands characterized by a bandwidth and a center frequency. Since the auditory cortex is tonotopically organized, the center frequency is related to the location while the bandwidth is related to the size of the area. The bandwidths of the frequency bands representing the areas in the cortex are dependent on the intensity of the auditory stimuli. Accordingly, empirical relations based on experiments can be used to model the bandwidth as a function of intensity.

Even if there is no actual external stimulus, i.e. there is no sound source, tinnitus causes an area in the auditory cortex to be activated so that a patient subjectively perceives a sound. The determined tinnitus bandwidth is the width of a frequency band that represents the tinnitus activation area in the auditory cortex.

There are different methods for determining the tinnitus bandwidth. In one embodiment, the tinnitus bandwidth may be calculated as the tinnitus frequency multiplied by a predetermined factor. The predetermined factor may be based on experimental and/or theoretical evaluations of the tinnitus bandwidth in relation to its center frequency.

In one preferred embodiment determining the tinnitus bandwidth comprises:

determining a tinnitus intensity as an intensity of the tinnitus perceived by the patient; and determining the tinnitus bandwidth according to a bandwidth defined by the frequency-discrimination threshold calibration at the determined tinnitus intensity.

In another embodiment, the tinnitus bandwidth may be determined on the basis of the audio-detection threshold calibration. It can be assumed that a reasonable approximation for the tinnitus bandwidth may be the bandwidth of a frequency band representing an actual sound with the same frequency, since it would activate a region in the cortex in the same location. When the bandwidth is modelled as a function of the intensity, as explained, a relation between frequency and intensity may be provided to determine the tinnitus bandwidth. Such a relation may be the audio-detection threshold calibration. Human beings have different hearing thresholds for different frequencies, meaning that the intensity that a sound must have in order to be perceived by the human ear varies depending on the frequency. The audio-detection threshold calibration thus represents the (preferably individual) hearing threshold for different frequencies (within a frequency range relevant for human hearing). Accordingly, an intensity parameter can be determined for the tinnitus based on the tinnitus frequency using the audio-detection threshold calibration. This intensity parameter is then used in the empirical relation linking the intensity to the bandwidth to obtain the tinnitus bandwidth.

The audio-detection threshold calibration may in some embodiments be obtained by testing the hearing level of the patient for a plurality of frequencies, preferably including the tinnitus frequency and the stimulation frequencies. In other words, the audio-detection threshold calibration may be specific for the patient. In other embodiments, a standard audio-detection threshold calibration may be used, wherein there may be a set of standard audio-detection threshold calibrations that are given by the average of measured curves for individuals with similar characteristics, such as age, gender, profession and so on. Different standard calibrations may also be used for hearing-impaired individuals, if there is e.g. a common underlying cause to the hearing loss.

After determining the parameters necessary for modelling the tinnitus activation area as a frequency band, which in turn represents a bandpass filter, similar parameters need to be determined to model the activation areas that one or more stimulation signals need to activate for treating tinnitus.

A stimulation frequency is determined by setting an offset from the tinnitus frequency, i.e. the stimulation frequency is always different from the tinnitus frequency and the difference or offset can be set according to a predefined offset parameter. The stimulation frequency, which is related to the location of the area activated by the stimulation signal, should be close enough to the tinnitus frequency in order to effectively treat tinnitus. The offset value may be decided so that the stimulation frequency lies in a conventional range for CR therapy. Possible values for a multiplicative offset (i.e. a ratio between the stimulation frequency and the tinnitus frequency) may be 1.2 or 1.1—positive offset—or 0.8 or 0.9—negative offset.

As mentioned above, the hearing threshold of the human auditory system depends on the frequency. In order for the stimulation signal to be perceived by the patient, the intensity of the stimulation signal must be at least above the hearing threshold for the specific stimulation frequency. Preferably, the intensity should exceed the hearing threshold by an amount that makes the stimulation signal clearly perceivable while being comfortable for the patient, i.e. not too loud. Such an amount, which may be determined based on human physiology, can be characterized as a predetermined intensity parameter. Accordingly, the stimulation intensity may be determined in one embodiment as the sum of the hearing threshold level corresponding to the stimulation frequency and the predetermined intensity parameter. The predetermined intensity parameter may be independent of frequency and could be in a range between 5 dB and 15 dB, preferably 10 dB.

Similarly to what is explained above for the determination of the tinnitus bandwidth, the stimulation bandwidth may be determined on the basis of the stimulation intensity by means of an empirical relation linking the bandwidth and the intensity. In particular, in some embodiments, the bandwidth may be considered to explicitly vary/depend only on the intensity as a first approximation. Although the bandwidth shows a dependence with frequency, this is rather weak, especially for typical tinnitus frequencies in the order of more than 5000 Hz. Accordingly, the bandwidth may be approximated to be a function exclusively of the intensity. However it should be noted that since the intensity is determined with the audio-detection threshold calibration, i.e. depends on the frequency, the individually determined (stimulation and/or tinnitus) bandwidth may have an implicit dependency on the frequency.

According to the invention, the stimulation frequency is adjusted to take into account the intensity of the stimulation signal, which affects the bandwidth, so that the location and the size of the area activated by the stimulation signal are optimized for therapeutic efficacy. In particular, a predefined overlap between the tinnitus activation area and the stimulation-activated area may be especially suitable for treating tinnitus, and this overlap between areas in the cortex can be translated into an overlap between the tinnitus frequency band and the stimulation frequency band. Accordingly, the initially chosen value of the stimulation frequency, which was based on a predetermined offset, is fine-tuned to achieve a predefined overlap.

In other words, modifying the stimulation frequency comprises modifying the offset of the stimulation frequency from the tinnitus and re-centering the stimulation bandwidth at the modified stimulation frequency.

Finally, the stimulation signal having the modified stimulation frequency and the determined stimulation intensity is generated. The term "stimulation signal" is used to denote both an electrical signal that is converted into an acoustic wave perceivable by a patient and an acoustic wave itself, which could be generated also in a different way. In one example, the generated stimulation signals are electrical signals whose amplitude represents a voltage. These electrical signals can be converted into sound by means of a transducer, e.g. a loudspeaker.

In some embodiments, the stimulation signal devised according to the method described above may nonetheless have a reduced efficacy if external factors interfere with the delivery of the stimulation signal. For example, a considerable intensity of an ambient noise may disturb the perception of the stimulation signal by the patient. The method may, thus, further comprise estimating an ambient noise level parameter e.g. via a microphone and modifying the stimulation intensity based on the ambient noise level parameter. Specifically, the stimulation intensity may be increased by an amount corresponding to the ambient noise level.

If the stimulation intensity is modified, the stimulation frequency may once again be adjusted to account for it. In particular, the stimulation bandwidth may be re-calculated based on the modified stimulation intensity and the stimulation frequency may again be modified to compensate for the different bandwidth and maintain the same amount of overlap.

If the ambient noise level decreases or increases further, additional adjustments of the stimulation frequency may be performed. The same applies if the tinnitus patient undergoes a modification of his hearing capabilities, meaning that the intensity contribution from the audio-detection threshold calibration is modified.

In a preferred embodiment, the method further comprises:
generating at least one secondary stimulation signal with a secondary stimulation frequency and a secondary stimulation intensity such that
the secondary stimulation intensity exceeds a hearing level of the patient, as defined by the audio-detection threshold calibration at the secondary stimulation frequency, by a predetermined quantity; and
the secondary stimulation frequency is offset from the tinnitus frequency by an amount greater than the offset of the primary stimulation frequency such that a secondary stimulation frequency band and the tinnitus frequency band overlap by a predetermined amount, wherein the secondary stimulation frequency band represents a frequency band centered at the secondary stimulation frequency and having a secondary stimulation bandwidth according to a bandwidth defined by the frequency-discrimination threshold calibration at the secondary stimulation intensity.

Preferably, generating the at least one secondary stimulation signal comprises:
determining at least one initial secondary stimulation frequency offset from the tinnitus frequency, wherein the offset of the at least one initial secondary stimulation frequency is greater than the offset of the at least one primary stimulation frequency;
determining the secondary stimulation intensity based on the at least one initial secondary stimulation frequency according to the audio-detection threshold calibration;
determining the secondary stimulation bandwidth as a bandwidth defined by the frequency-discrimination threshold calibration at the secondary stimulation intensity;
modifying the at least one secondary stimulation frequency so that the primary stimulation frequency band and a modified secondary stimulation frequency band overlap by the predetermined amount, wherein the modified secondary stimulation frequency band represents a frequency band with the determined secondary stimulation bandwidth centered at the modified secondary stimulation frequency; and
generating the at least one secondary stimulation signal based on the modified secondary stimulation frequency and the secondary stimulation intensity.

In other words, the method may further comprise determining at least one secondary stimulation frequency offset from the tinnitus frequency, wherein the offset of the at least one secondary stimulation frequency is greater than the offset of the at least one primary stimulation frequency; determining at least one secondary stimulation intensity based on the at least one secondary stimulation frequency according to the audio-detection threshold calibration; determining at least one secondary stimulation bandwidth as the width of at least one secondary stimulation frequency band centered at the at least one secondary stimulation frequency on the basis of the at least one secondary stimulation intensity; modifying the at least one secondary stimulation frequency on the basis of the at least one primary stimulation frequency, the at least one primary bandwidth and the at least one secondary stimulation bandwidth so that the at least one secondary stimulation frequency band and the at least one primary stimulation frequency band overlap by the predetermined amount; generating at least one secondary stimulation signal based on the modified at least one secondary stimulation frequency and the at least one secondary stimulation intensity; and optionally delivering to the patient the at least one primary stimulation signal and the at least one secondary stimulation signal to treat the patient's tinnitus.

In other words, the primary stimulation signals are signals whose activated zones overlap directly with the tinnitus activation area, while for secondary stimulation signals the activated zones do not overlap directly with the tinnitus activation area. For these "second-neighbors" the method explained above may also be applied with the difference that the overlap is with the primary stimulation frequency bands.

In one aspect multiple therapeutic stimulations signals, specifically as provided in one of the embodiments described herein are provided for use in a stimulation of the auditory cortex, wherein the frequency of each stimulation signal is adjusted based on the intensity of the stimulation signal. The multiple therapeutic stimulations signals are preferably provided for use in treating tinnitus.

In another aspect, the invention provides a system or device configured to provide stimulation signals for acoustic coordinated reset neuromodulation therapy, the system or device comprising:
means for providing an audio-detection threshold calibration, which defines a frequency dependent hearing level of the patient;
means for providing a frequency-discrimination threshold calibration, which defines an intensity dependent bandwidth of frequencies not discriminable by the patient;
means for evaluating a tinnitus frequency for tinnitus experienced by a patient;
means for determining a tinnitus bandwidth as the width of a tinnitus frequency band centered at the tinnitus frequency; and
means for generating at least one first primary stimulation signal with a first primary stimulation frequency and a first primary stimulation intensity such that
 the first primary stimulation intensity exceeds a hearing level of the patient, as defined by the audio-detection threshold calibration at the first primary stimulation frequency, by a predetermined quantity; and
 the first primary stimulation frequency is offset from the tinnitus frequency such that a first primary stimulation frequency band and the tinnitus frequency band overlap by a predetermined amount, wherein the first primary stimulation frequency band represents a frequency band centered at the first primary stimulation frequency and having a first primary stimulation bandwidth according to a bandwidth defined by the frequency-discrimination threshold calibration at the first primary stimulation intensity.

Preferably, the system or device is adapted to perform a method according to the present invention, specifically in accordance with one or more of the preferred embodiments described herein.

In yet another aspect, the present invention provide a computer program product, such as storage medium or a signal stream or preferably digital signals, comprising computer readable code, which when loaded and executed by a computer system, causes the computer system to perform operations according a method of the present invention, specifically in accordance with one or more of the preferred embodiments described herein.

According to some preferred implementations, generating the at least one primary and/or secondary stimulation signal, specifically determining the at least one primary and/or secondary stimulation frequency and the respective intensity is described as an iterative (preferably numerical) process based on a predetermined or individual model for the dependency of an auditory filter bandwidth from the signal intensity (and eventually the signal frequency) and preferably based on an individual measurement of the hearing loss (audiogram). Alternatively, a parameterized analytical model can be used for the auditory filter bandwidth (i.e. the frequency-discrimination threshold calibration) and its dependency from the signal intensity (and eventually the signal frequency) together with a parametrized analytical model of the audiogram (i.e. the audio-detection threshold calibration) such that the desired stimulation frequencies and the intensities can preferably be expressed as an (explicit) analytical term depending on the parameters of the models for the frequency-discrimination threshold calibration and the audio-detection threshold calibration. Generating/determining the stimulation signal(s) may then include a fitting process for the parameters of said models to determine the stimulation frequency and intensity based on that analytical term.

Further embodiments are disclosed herein or will become apparent to those skilled in the art after having read and understood the specification and drawings hereof.

DETAILED DESCRIPTIONS OF SOME EMBODIMENTS

Described herein are various embodiments of systems, devices, components and methods relating to acoustic coordinated reset medical neuromodulation therapies delivered to patients via external and/or implanted systems, devices and components.

In the following the terms "stimulation signal" and "stimulation tone" will be used interchangeably.

Figure 1:
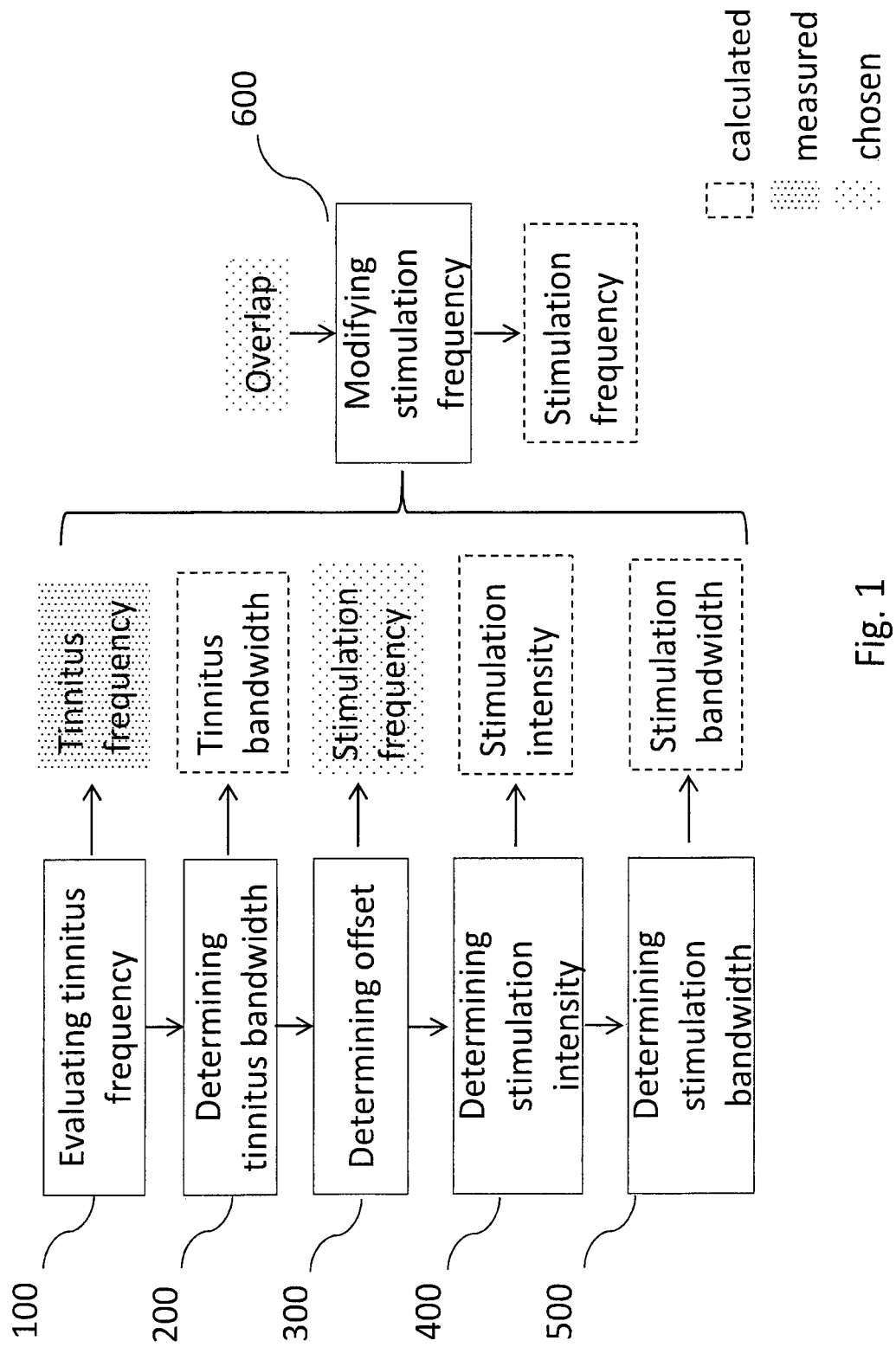
FIG. 1 shows a schematic representation of an exemplary method for acoustic CR neuromodulation according to the invention.

We refer first to the following general overview and information regarding the human auditory system, particularly in relation to the tinnitus phenomenon, various aspects of which find application in one or more of the embodiments described and disclosed herein.

The basilar membrane within the cochlea of the inner ear has a tonotopic structure, meaning that each one of different locations spatially situated along the membrane is particularly sensitive to a specific frequency. Accordingly, the basilar membrane may be modeled as an array of overlapping band-pass filters that are called auditory filters. The band-pass filters are characterized by a bandwidth, wherein sounds having frequencies within the bandwidth of a given auditory filter are not well discriminated as different sounds and interfere with each other. Conventionally the upper and lower cut-off frequencies defining the bandwidth are defined as the points where the intensity falls to 3 dB below the peak amplitude.

Although the auditory filters are not the same for different frequencies, different intensities and different individuals, a typical auditory filter of a normal ear is preferably distinguishable from a typical auditory filter of a hearing-impaired ear. In particular, the Q factor, which is defined as the ratio between the central frequency and the bandwidth, of a normal ear and of a hearing-impaired ear for the same central frequency is lower for the hearing-impaired ear.

The shape of the auditory filter is determined by means of psychoacoustic tuning curves, which show a subject's threshold for detection of a pure tone when a masking tone is played to the subject at the same time as the pure tone. In particular, it is measured which level of intensity is needed for a masking tone to eliminate the perception of the pure tone.

The complex shape of an auditory filter can be approximated by a rectangular frequency band characterized by an equivalent rectangular bandwidth (ERB). The ERB is such that the rectangular frequency band passes the same amount of energy as the auditory filter that it approximates.

The basilar membrane is part of the peripheral auditory system and the auditory sensory information is carried from the ear to the auditory cortex by afferent auditory nerve fibers. The tuning curves of the nerve fibers are expected to correspond to the tuning curves obtained from a specific location on the basilar membrane, because each afferent nerve fiber innervates a single inner hair cell, which in turn is aligned with a single location on the membrane. The tinnitus sensation is caused by deafferentation, i.e. the interruption or destruction of the afferent connections, and the size of deafferentation can be measured via the tuning curves. Accordingly, it can be assumed that the size of the area of cortex activation is also related to the shape of the tuning curves and, in particular, to the bandwidths.

Specifically, since the bandwidth increases with increasing intensity of a sound, the activation area in the cortex is bigger for a tone with higher intensity. The intensity of a sound is the amount of energy transported by a sound wave propagating in a medium past a given area of the medium per unit of time. The faintest sound that the typical human ear can detect has an intensity of about $1*10^{-12}$ W/m$^2$, which defines the threshold of hearing. The scale for measuring intensity is the decibel (dB) scale, in which the threshold of hearing is assigned a value of zero. The intensity of sound can be expressed in dB HL (hearing level), where the sound pressure is expressed with respect to the hearing threshold of a normal hearing subject (see, for example, ISO 389). The actual hearing level threshold for a specific case depends on many factors such as age of the subject and ambient noise.

As explained, the size of an activation area in the cortex is proportional to the intensity of an acoustic stimulus. In order to provide an optimal desynchronizing effect of the stimulation signals for treating tinnitus the areas activated by the stimulation signals in the cortex should overlap by predefined amounts. For example, it has been found that an overlap of about 30% among neighboring areas provide considerable therapeutic benefit to the patient.

Until now CR therapy tones have been fixed and selected with respect to the tinnitus pitch without considering that increased stimulation tone intensities lead to wider activation areas. Currently used tones are only optimal for a particular intensity band. If the stimulation tone intensity needs to be adjusted outside the standard or conventional range (e.g., because of individual hearing thresholds or a noisy environment), stimulation tones can become suboptimal and therapeutic outcome for patients can be reduced.

According to the invention, the selection of the frequencies and intensities for CR stimulation signals is optimized by adapting the spread of the therapeutic frequencies on the basis of to the intensity of each of the individual tones, as well as optionally with respect to the hearing thresholds of the patient being treated.

Acoustic CR neuromodulation should be applied slightly above an individual patient's hearing threshold. Let us assume that acoustic CR neuromodulation should be applied X dB above the hearing threshold of an individual patient. Hence, a normal hearing subject with no hearing loss would need a stimulation level of X dB, but a hearing impaired subject having a hearing loss of Y dB HL at a given stimulation frequency would require a stimulation level of (X+Y) dB HL.

We know from the example of Hopkins and Moore (2011) that the perception of sound changes with signal level in dB HL. This information can be used to configure the spacing of the stimulation signals across a frequency scale with respect to the stimulation intensity or signal level actually required to realize a stimulation tone X dB above an individual hearing threshold.

If the patient changes the intensity of the stimulation signal, or the intensity is changed automatically by the device delivering the stimulation, the frequencies of the stimulation tones are changed and/or adapted accordingly (i.e., stimulation tone frequencies are changed if the stimulation intensity is modified). No fixed stimulation signal is programmed. Instead, a stimulation algorithm utilizing dB hearing loss (HL) information from a patient assessment and current master volume settings are used to instantaneously define optimal stimulation frequencies. A thresholdogram obtained during the patient assessment is stored and used by an algorithm such that for any set of frequencies a balanced set of stimulation tones can be defined. For high intensity stimulation applications, a wide spread of stimulation tones may be required.

A thresholdogram may be obtained during patient assessment and stored for use by the algorithm such that for any frequencies a balanced set of stimulation tones can be defined. Using such techniques, the algorithm/software can determine the appropriate intensity (dB HL for the individual patient) corresponding to each of the stimulation tones. For each stimulation tone, the optimal frequency in relation to the pitch frequency (tinnitus frequency) is calculated. The frequency of the stimulation tone is then re-adjusted and the local amplitude requirements are checked again. Using such an iterative process, stimulation frequency and amplitude levels are optimized. For higher-intensity stimulation applications a wider spread of stimulation tones may be required. An example of stimulation tones and how they are calculated is set forth below.

In addition, patient feedback may be recorded and then employed to adjust or change therapeutic stimulation signal center frequencies, therapeutic stimulation signal intensities, amounts of overlap between therapeutic stimulation signals, and/or therapeutic stimulation signal bandwidths.

Based on a current stimulation intensity (dB above threshold), stimulation frequencies can be changed instantaneously or nearly instantaneously. Some type of inertia or delay may be employed to avoid over-rapid adjustments in stimulation intensity delivered to the patient. Using such techniques, an iPod configured to carry out the methods described herein can be programmed and configured to automatically adjust the intensity of the delivered stimulation, and no intervention by the patient is required. Together with automatic adaptation of the stimulation frequencies, stimulation is optimized and stimulation outcomes are improved. In one embodiment, a stimulation adaptation algorithm is configured to enable programming automated stimulation frequency adjustments based on an above-threshold dB level of stimulation.

FIG. 1 shows a schematic representation of an exemplary method for acoustic CR neuromodulation according to the invention. The method will be described also with reference to FIGS. 2 to 6.

In step 100 the tinnitus frequency $f_T$ is evaluated. Tinnitus is the subjective perception of a sound in the absence of actual sound waves. Although it is a subjective condition, there are clinical ways to objectively measure its audiometric qualities, such as frequency and intensity. The tinnitus sound as experienced by the patient may e.g. be a pure tone, a harmonic tone or a noise and the frequency of the tinnitus would be the frequency of the pure tone, the fundamental frequency of the harmonic tone or the center frequency of the noise, respectively.

The tinnitus frequency $f_T$ may be evaluated according to the pitch matching method described in the paper "Validation of a Mobile Device for Acoustic Coordinated Reset Neuromodulation Tinnitus Therapy" by Hauptmann et al., 2016. The tinnitus frequency evaluation may enable a quantitative description of the perceived tinnitus sound via a numerical value for the tinnitus frequency $f_T$, which may be expressed in Hz.

Figure 2:
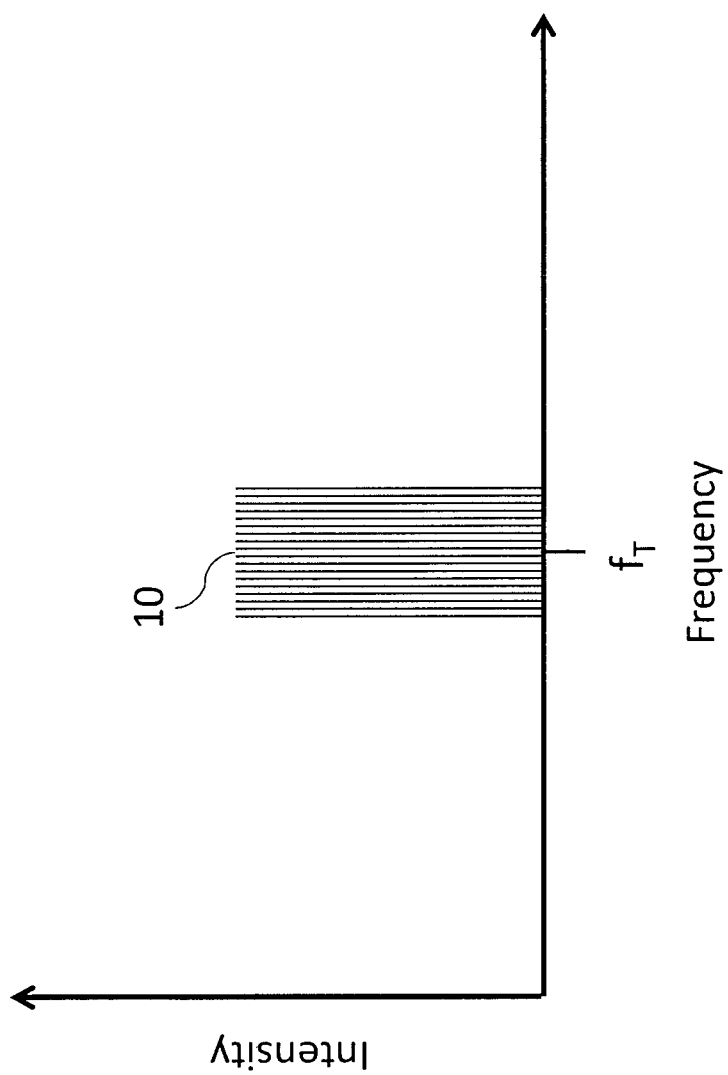
FIG. 2 shows an exemplary tinnitus frequency band.

In step 200 the tinnitus bandwidth is determined, wherein the tinnitus bandwidth is the width of a tinnitus frequency band centered at the tinnitus frequency $f_T$. An example of a tinnitus frequency band 10 is shown in FIG. 2 in an intensity-frequency plane, wherein the frequency is expressed in Hz and the intensity in dB. The representation of FIGS. 2 to 6 is only schematic and that is why no values are shown on the axes.

The width of the band 10 represents the bandwidth for an auditory filter relative to the tinnitus frequency $f_T$. As explained above, the auditory filter bandwidth is a valid approximation for the size of an area activated in the auditory cortex. In some examples, the bandwidth of the band 10 is an ERB.

The height of the band 10 may represent a tinnitus intensity parameter that does not, however, necessarily reflect a perceived loudness of the tinnitus. Indeed, for the tinnitus frequency band 10, a determination of the vertical dimension is not necessary and the height could take any value in the representation. Only the bandwidth of the tinnitus frequency band 10 is needed for optimally selecting the frequencies of the stimulation signals. In some cases, determination of the bandwidth is based on a tinnitus intensity parameter, in other cases not, as explained below.

It can be seen that the tinnitus frequency band 10 is centered on the tinnitus frequency $f_T$ as evaluated in step 100. The bandwidth $ERB_T$ of the tinnitus frequency band 10 may be determined in different possible ways.

According to one example, the bandwidth $ERB_T$ of the tinnitus band 10 may be calculated from the central frequency $f_T$, e.g. by means of a proportionality factor. The proportionality factor may be a constant factor p or a factor that is a function of the frequency, p(f), so that $ERB_T = p/f_T$ or $ERB_T = p(f_T)/f_T$. For example p may be 0.15 or 0.2 or 0.25.

The proportionality factor may be determined according to empirical relations based on past deliveries of the CR therapy.

In another example, determining the bandwidth $ERB_T$ requires first a determination of a tinnitus intensity parameter. The tinnitus intensity parameter may be determined similarly to the stimulation intensity (see below) on the basis of an audiogram and a predetermined intensity parameter. However, while the stimulation intensity may be used when actually delivering the stimulation signals to the patient, the tinnitus intensity parameter is a functional parameter that models a size of the tinnitus activation area and may or may not correspond to tinnitus loudness as perceived by the patient. Also the tinnitus bandwidth $ERB_T$ may be determined similarly to the stimulation bandwidth on the basis of the tinnitus intensity, as explained below for the stimulation bandwidth.

Figure 3:
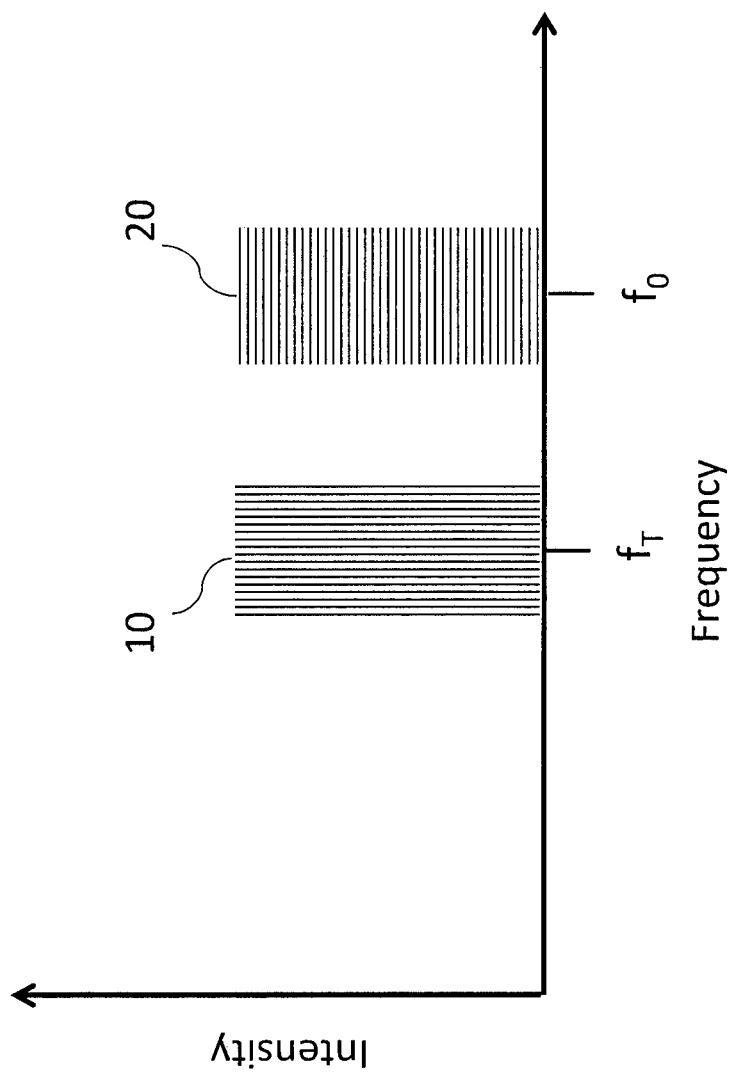
FIG. 3 shows an exemplary stimulation frequency band.

After determining the tinnitus bandwidth, which can be either calculated from the tinnitus frequency or from the tinnitus intensity parameter, central frequency, intensity and bandwidth for a stimulation frequency band are determined (steps 300, 400 and 500 of FIG. 1). An example of a stimulation frequency band 20 is shown in FIG. 3.

In step 300, an initial offset from the tinnitus frequency $f_T$ is determined to obtain the stimulation frequency $f_0$. This initial stimulation frequency $f_0$ is only a starting point for the optimization process herein described and, thus, does not necessarily coincide with the stimulation frequency $f_1$ that will actually be used for the stimulation signal. The stimulation frequency has a chosen, predetermined value $f_0$ that is usually later adjusted to become $f_1$, for which the area activated by the stimulation signal in the cortex yields the best therapeutic effect, as explained below.

This initial offset may be an educated guess for a value that lies in the vicinity of the tinnitus frequency $f_T$, as required by the CR therapy. For example, the stimulation frequency $f_0$ may be given by 1.3 $f_T$, or 1.2 $f_T$ or 1.1 $f_T$, in case of a positive offset as shown in FIG. 3, or may be given by 0.7 $f_T$, 0.8 $f_T$ or 0.9 $f_T$, in case of a negative offset.

In step 400, the stimulation intensity is determined. The stimulation intensity should be understood as the intensity at which the stimulation signal should be delivered to the patient in order for it to be correctly perceived and to effectively treat the tinnitus. Accordingly, the stimulation intensity should be at least above the hearing threshold of the patient and usually be greater than the hearing threshold level by a given interval. In other words, the stimulation intensity can be computed as the sum of two terms, the first term being the hearing threshold level and the second term being a predetermined intensity parameter.

Such a predetermined intensity parameter could be based on the human physiology in general and/or on considerations related to the equipment through which the stimulation signal is going to be delivered to the patient, e.g. headphones or loudspeaker: For example the predetermined intensity parameter may range from about 5 dB to about 15 dB, and preferably be 10 dB.

Figure 8:
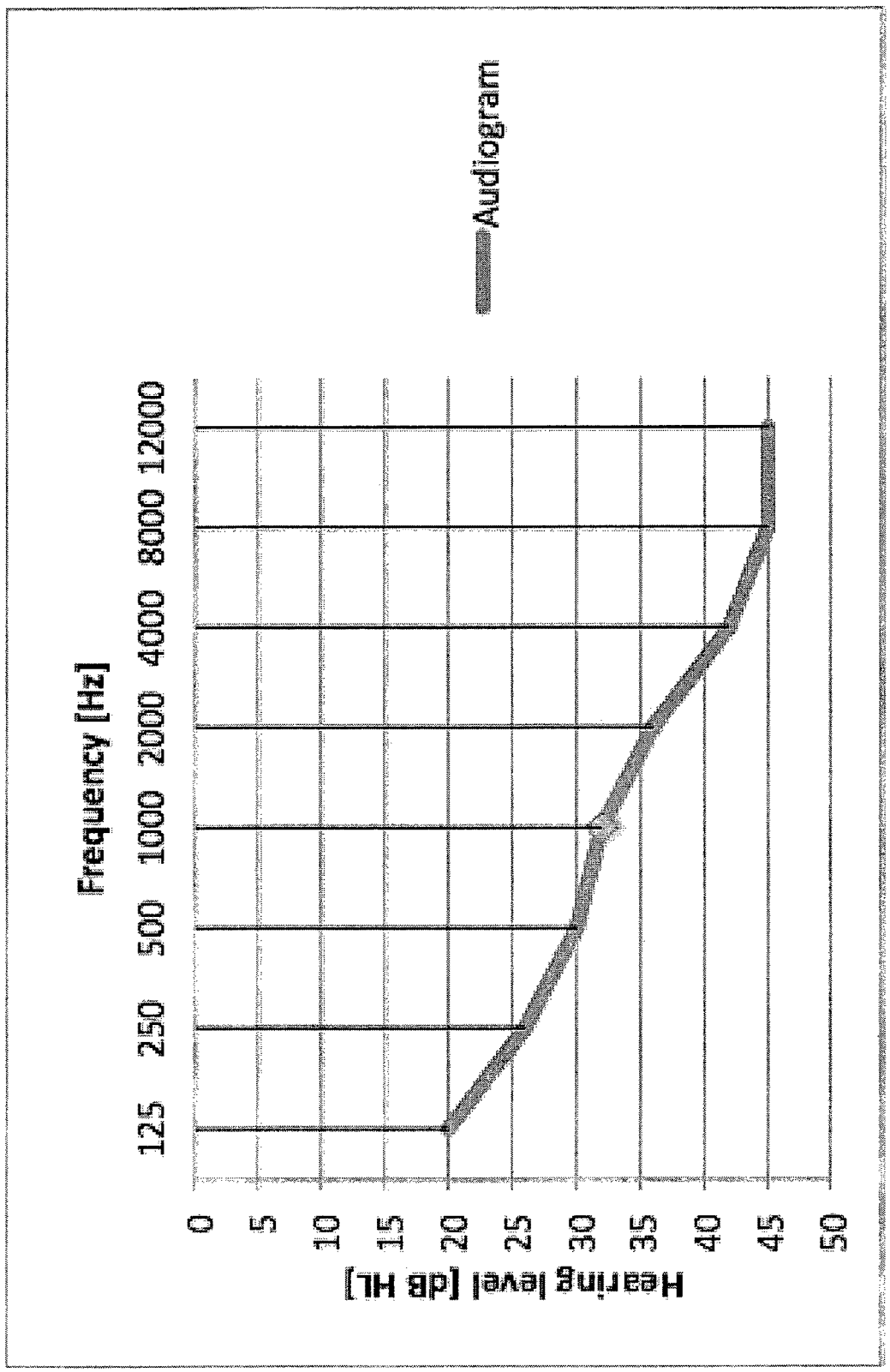
FIG. 8 shows an exemplary audiogram.

The hearing threshold is taken from a thresholdogram as mentioned above and is frequency-dependent. An example of a thresholdogram, also called audiogram, is shown in FIG. 8. It can be seen that the hearing level, in dB, varies of more than 20 dB across a frequency range spanning frequencies in the order of 100 Hz to frequencies in the order of 10000 Hz.

To summarize, the stimulation intensity is calculated on the basis of the individual hearing threshold of the patient at the stimulation frequency $f_0$ (as measured) and a chosen predetermined intensity parameter.

In step 500 the stimulation bandwidth is determined. The width of the stimulation frequency band 20 represents the bandwidth for an auditory filter relative to the stimulation frequency $f_0$ and also the size of the area that will be activated by a stimulation signal with stimulation frequency $f_0$ and corresponding stimulation intensity. Exemplarily, the bandwidth of the stimulation frequency band 20 is an ERB.

In particular, as explained above, the bandwidth increases with increasing intensity of a sound. More generally, the bandwidth of an auditory filter is directly dependent both on the intensity and the frequency of a tone. However, it has been found that the frequency dependence is negligible in first approximation for high frequencies, which is the case of the tinnitus. For example, in Glasberg & Moore "Derivation of auditory filter shapes from notched-noise data," Hear. Res. 47, 103-138, 1990 the following approximation was found for the dependence of the relative ERB (i.e. normalized to the center frequency of the band): ERB/24.7−1/f=4.37. This approximation shows a weak, inversely proportional dependence with respect to the frequency.

The relative ERB is typically in the range from 0.15-0.30 (Hopkins & Moore 2011), hence the first factor is in the range of 0.006-0.012. For frequency ranges where tinnitus is mostly observed, e.g. frequencies of 8000 Hz, the second factor is 1/8000, namely 0.000125. So the correction is 1-2%, which can be neglected for the sake of simplification.

Accordingly, in this exemplary embodiment the direct dependency of the bandwidth on the frequency will be partially accounted for by considering the relative ERB but other corrections will be neglected. The stimulation bandwidth as relative ERB is considered to be only a function of the intensity. However, since the intensity is calculated based on the frequency, there is still an indirect dependence of the relative ERB on the frequency.

Hopkins & Moore, "The effects of age and cochlear hearing loss on temporal fine structure sensitivity, frequency selectivity, and speech reception in noise", Ac. Soc. of America, 334-349, 2011 found an exponential model to describe the dependency of the relative ERB on the intensity, namely $$\text{ERB} = 0.138 \exp(0.011\ S),$$

where S is the intensity of the acoustic signal in dB. Accordingly, the stimulation bandwidth is calculated using the above formula with respect to the stimulation intensity.

In FIG. 3 it can be seen that the stimulation frequency band 20 is initially centered on the stimulation frequency $f_0$ as calculated in step 300. The height of the band 20 in the intensity-frequency plane represented the stimulation intensity as calculated in step 400. The bandwidth ERBs of the stimulation frequency band 20 is calculated as described for step 500 above.

In step 600 of FIG. 1 the stimulation frequency is modified. Specifically, as mentioned before, the chosen value $f_0$ is adapted to a new value $f_1$ so that the stimulation signal activates an area in the cortex that provides maximal therapeutic benefit. Such a benefit is achieved when the activation area of the stimulation signal has a partial overlap with the tinnitus activation center: Since, as explained, the size of these areas is modelled by the bandwidths of the frequency bands, the adjusted value $f_1$ for the stimulation frequency is the value for which the overlap has a desired, predetermined value. In other words, given the estimated tinnitus frequency $f_T$, the calculated tinnitus relative bandwidth $\text{ERB}_T$ and the calculated stimulation relative bandwidth ERBs, the value $f_1$ may be found by solving the equation:

$$\frac{\left(f_T + \frac{f_T \cdot ERB_T}{2}\right) - \left(f_1 - \frac{f_1 \cdot ERB_S}{2}\right)}{f_T \cdot ERB_T} = L, \quad (1)$$

if the initial offset for $f_0$ was positive and $$\frac{\left(f_1 + \frac{f_1 \cdot ERB_S}{2}\right) - \left(f_T - \frac{f_T \cdot ERB_T}{2}\right)}{f_T \cdot ERB_T} = L, \quad (2)$$

if the initial offset for $f_0$ was negative, wherein L is a predetermined overlap parameter in the range between 0% and 100%. Please note that in the above equations the size of overlap has been considered with respect to the tinnitus bandwidth $f_T \cdot ERB_T$, however different choices are possible, e.g. the stimulation bandwidth or a fixed predetermined value. L could be in the range between about 20% and about 40%, in particular 30%, as found by Lysyansky et al., 2013.

Figure 4:
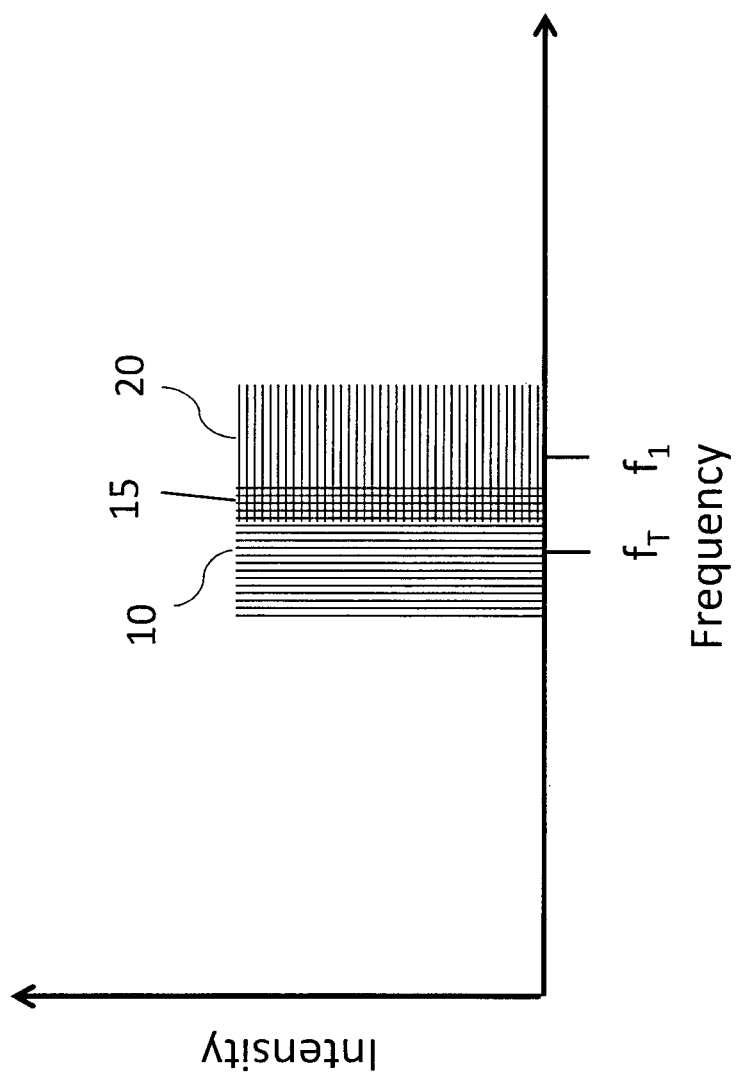
FIG. 4 shows an exemplary overlap between the tinnitus frequency band and the stimulation frequency band.

FIG. 4 shows the overlap region 15 between the tinnitus frequency band 10 and the stimulation frequency band 20, which is now centered around the new, modified stimulation frequency $f_1$.

Figure 5:
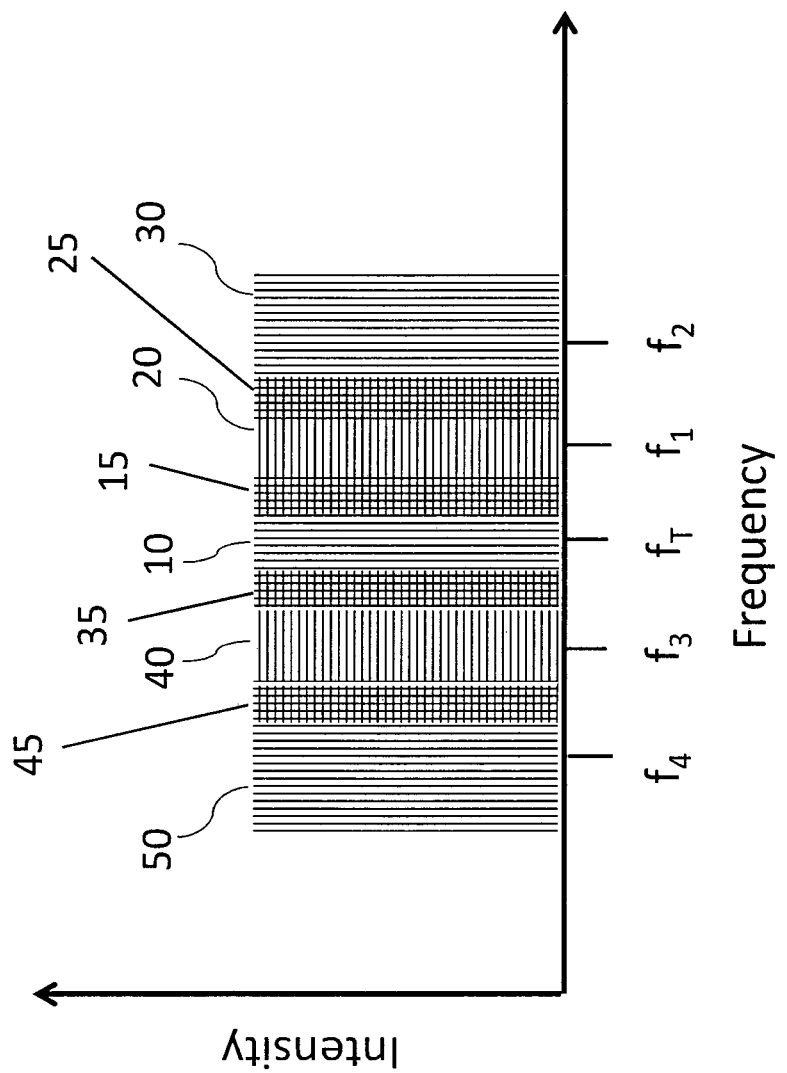
FIG. 5 shows an exemplary plurality of stimulation frequencies bands.
Figure 6:
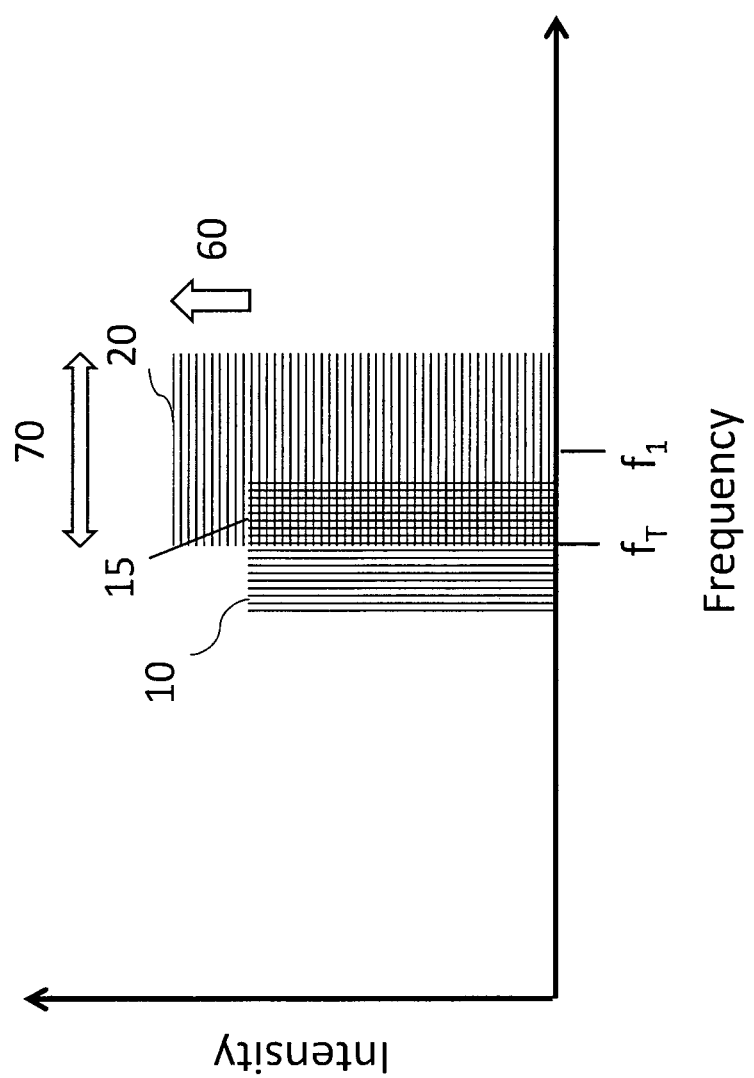
FIGS. 6 and 7 show an exemplary stimulation frequency band modified for ambient noise.

FIG. 5 shows an exemplary embodiment in which four stimulation signals are employed, whose respective frequency bands are illustrated in the figure. The procedure for determining the stimulation frequency $f_3$ is identical as the one described so far for $f_1$, with the only difference that the original offset for $f_3$ was negative. Accordingly, equation (2) above should be used to determine the position of the stimulation frequency band 40 so that it overlaps by a predetermined amount 35 with the tinnitus frequency band 10. The stimulation signals corresponding to stimulation frequency bands 20 and 40 may be called primary stimulation signals because they activate zones in the cortex that lie directly adjacent and overlap with the tinnitus activation area.

The stimulation signals corresponding to stimulation frequency bands 30 and 50 may be called secondary stimulation signals because their activated zones do not overlap directly with the tinnitus activation area. The procedure for determining frequencies $f_2$ and $f_4$ is basically the same as the method described above, with the only difference that the overlap zones 25 and 45 are determined with respect to the primary stimulation frequency bands and not to the tinnitus frequency band. Thus, $f_1$ must be determined before $f_2$ and $f_3$ must be determined before $f_4$.

FIG. 5 shows that all the stimulation frequency bands have the same intensities. In some embodiments, it may be desired that all stimulation signals are delivered with the same intensity, but there may also be different intensities in other embodiments. It is worth noting that the bandwidths of the stimulation frequency bands are not necessarily the same, even if the intensities are the same and the Hopkins & Moore approximation is used for calculating the bandwidths, without an explicit frequency dependency. The reason is that, as explained, there is an implicit frequency dependence due to the fact that the intensities are calculated based on an audiogram with frequency-dependent intensity values.

A real life example with numerical values on the basis of the heretofore disclosed method will be described in the following for two primary stimulation signals.

Table 1 below shows the input values for the computations of the method, which include the patient audiogram, the evaluated tinnitus frequency, the predetermined overlap parameter, the predetermined intensity parameter and the initial offsets for the stimulation frequencies.

TABLE 1

| Input | |
|---|---|
| Tinnitus frequency | 6354 Hz |
| Overlap parameter | 30% |
| Intensity parameter | 10 dB |
| Offset values | 0.8 $f_T$, 1.2 $f_T$ |
| Audiogram | 125 Hz - 20 dB |
| | 250 Hz - 26 dB |
| | 500 Hz - 30 dB |
| | 1000 Hz - 32 dB |
| | 2000 Hz - 36 dB |
| | 4000 Hz - 42 dB |
| | 8000 Hz - 45 dB |
| | 12000 Hz - 45 dB |

Table 2 is obtained from Table 1 as explained below:

TABLE 2

| Intermediate calculated values | | |
|---|---|---|
| Frequency (Hz) | Intensity (dB) | Relative ERB |
| 6354 | 53.8 | 0.249 |
| 5083.2 ($f_{02}$) | 52.8 | 0.247 |
| 7624.8 ($f_{01}$) | 54.7 | 0.252 |

The frequency values $f_{01}$ and $f_{02}$ are obtained from the tinnitus frequency and the offset values and are the initial chosen values for the stimulation frequencies.

The intensity values are obtained by interpolating the audiogram to obtain a hearing level for the calculated frequency values $f_{01}$ and $f_{02}$ and also for the tinnitus frequency $f_T$. The intensity parameter of 10 dB is then added to the audiogram value to arrive at the values in the second column of Table 2.

The relative ERB values in the third column of Table 2 are calculated using the Hopkins & Moore exponential model on the basis of the intensities in column two.

Finally, the adjusted values for the stimulation frequencies $f_1$ and $f_2$ are calculated to achieve the overlap factor of Table 1 e.g. using equations (1) and (2) above, respectively, and are reported in Table 3 below.

TABLE 3

| Frequencies for stimulation signals. | |
|---|---|
| Frequency (optimized) | Offset (optimized) |
| $f_1$ 7632.2 | 1.201 |
| $f_2$ 5374.3 | 0.846 |
| $f_3$ 9172.2 | 1.444 |
| $f_4$ 4548.1 | 0.716 |

The modified frequencies on the basis of the overlap parameter have a corresponding modified new offset with respect to the tinnitus frequency.

The third and fourth row of Table 3 show also values for frequencies $f_3$ and $f_4$ for the exemplary embodiment of FIG. 5, which are determined using as constraint an overlap factor of 30% (see Table 1) for the overlapping areas 25 and 45 between the third and fourth stimulation frequency bands 30 and 50 and the first and second stimulation frequency bands 20 and 40, respectively.

The predetermined intensity parameter discussed above is based on quality of hearing considerations. If there is a change in the conditions in which the stimulation signal is delivered to a patient that affects the perception of the patient, e.g. ambient noise, the quality of hearing and consequently the efficacy of the therapy may be diminished. Accordingly, an additional input parameter that characterizes the ambient noise level may be introduced. Means for detecting an ambient noise level, such as a microphone, may be provided.

The stimulation intensity may need to be re-determined to take into account the ambient noise level parameter. Looking at FIG. 6, the increase in the intensity, which corresponds to the ambient noise level that must be compensated for, is indicated by the arrow 60. However, since the bandwidth depends on the intensity, there is an additional modification indicated by the arrow 70, namely the bandwidth increases as well. It can be seen that the overlap 15 is now accordingly larger than in FIG. 4 and may be not optimal for the therapy.

Figure 7:
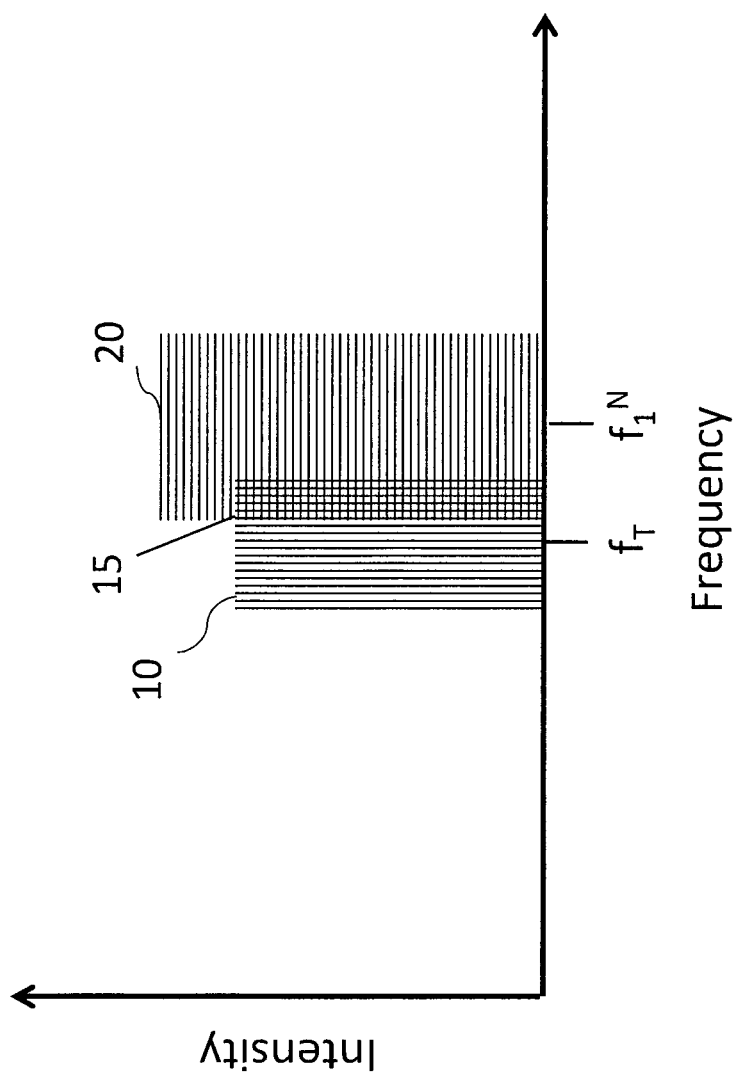

Consequently, the optimization step may be applied again to find an adjusted stimulation frequency $f_1^N$. In other words, the stimulation frequency may be once again modified on the basis of the tinnitus frequency, the tinnitus bandwidth and the modified stimulation bandwidth to maintain the desired amount of overlap. The result is shown in FIG. 7.

If an ambient noise level parameter of 10 dB is added to the inputs of Table 1, the values in Tables 2 and 3 are modified as shown in Tables 4 and 5, respectively.

TABLE 4

| Intermediate calculated values with ambient noise. | | |
|---|---|---|
| Frequency (Hz) | Intensity (dB) | Relative ERB |
| 6354 | 63.8 | 0.278 |
| 5083.2 ($f_{02}$) | 62.8 | 0.275 |
| 7624.8 ($f_{01}$) | 64.7 | 0.281 |

TABLE 5

| Frequencies for stimulation signals with ambient noise. | |
|---|---|
| Frequency (optimized) | Offset (optimized) |
| $f_1$ 7805.2 | 1.228 |
| $f_2$ 5274.1 | 0.830 |
| $f_3$ 9593.1 | 1.510 |
| $f_4$ 4380.5 | 0.689 |

It can be seen that louder tones require stimulation frequencies more spread out. This is the case in presence of ambient noise but also for hearing-impaired subjects, whose intensity values in the audiogram are higher for a given frequency with respect to a normal subject.

In one embodiment, as shown above, four therapeutic frequencies are designed to activate different areas of the central auditory system in a coordinated manner. Note that that fewer or more such tones may be employed, in upper and lower frequency pairs or otherwise (e.g. singly or in combinations of odd and/or even numbers). The various embodiments include those where one therapeutic stimulation signal is employed, two stimulation signals are employed, three therapeutic stimulation signals are employed, four therapeutic stimulation signals are employed, five therapeutic stimulation signals, six therapeutic stimulation signals are employed, and so on.

It is also to be understood that equivalent rectangular bandwidths (or ERBs) are only a particular type of auditory filter bandwidth (or AFB).

Although an amount of overlap of about 30% between frequencies or tones has been discovered to provide good results, other amounts of overlap between frequencies or tones such as about 10% overlap, about 15% overlap, about 20% overlap, about 25% overlap, about 35% overlap, about 40% overlap and about 50% overlap are also contemplated in the various embodiments. Further, the amount of overlap needs not be the same for all frequency bands. 12. For example, the predetermined amount overlap is preferably in the range of about 2% to about 40% of the tinnitus frequency band, preferably in the range of about 5% to about 35% of the tinnitus frequency band, more preferably in a range of not more than about 30% of the tinnitus frequency band, most preferably in a range of not more than about 25% of the tinnitus frequency band.

As shown in the preceding pages, some of the calculations, methods, algorithms, equations and/or formulas used to calculate or determine specific tones or frequencies, auditory filter bandwidths (including equivalent rectangular bandwidths or EBRs), the amount of overlap between adjoining tones or frequencies, and/or the intensity of stimulation that is to be delivered to a patient are derived in part from published sources (e.g., Hopkins and Moore, 2011).

It is to be understood that these calculations, methods, algorithms, equations and/or formulas are merely illustrative, and that other suitable calculations, methods, algorithms, equations and/or formulas may be employed to attain the same, or substantially the same, results.

In Hopkins and Moore, 2011, the perception of sound under different situations, and in particular for different sound intensity levels, is studied. Therapeutic stimulation is not a topic of this article. One equation from Hopkins and Moore, 2011, is herein employed to design an effective therapeutic stimulation regime for reducing the effects of tinnitus. This equation is used to space therapy tones apart from one another such that distinct sub-populations of the neuronal network are stimulated by each of the four stimulation tones, which is intended to provide an optimal desynchronizing effect of the stimulation and accordingly provide maximum therapeutic benefit to the patient.

One of the key issues explored in Hopkins and Moore, 2011 is the effect of human hearing loss and age on frequency selectivity. One portion of the study presented by Hopkins and Moore, 2011, provides an intuitive mathematical formula that enables rapid estimation of auditory filter bandwidths to permit further investigation of the correlation between human hearing loss and age on the one hand, and frequency selectivity on the other hand. In one embodiment, we apply the formula of Hopkins and Moore, 2011, to permit fine tuning of a pre-existing acoustic stimulus therapy for tonal subjective tinnitus. That is, we do not apply the formulae disclosed by Hopkins and Moore, 2011, to research frequency selectivity in humans. Instead, we calculate one AFB and/or ERB for below the tinnitus frequency and one AFB and/or ERB for above the tinnitus frequency. We use these approximations for an overlap calculation of tones or frequencies 1 through 4. By doing so we avoid the need to perform numerous iterations that would likely not improve precision or therapeutic performance by very much (but which according to some embodiments may be carried out).

Moreover, in some embodiments the order in which AFB and/or ERBs and stimulation intensities are calculated may be reversed, since in the general case the intensity of the stimulation tones is obtained before the AFB and/or ERBs can be calculated. Consequently, the expected intensity of the stimulation tones can be approximated initially and iteratively as a final intensity of stimulation is initially unknown.

Upon having read and understood the specification and claims of the present patent application, those skilled in the art will immediately understand and appreciate that other mathematical equations and formulas, or modified mathematical equations and formulas, may be employed advantageously to attain the same or substantially the same results without departing from the scope and spirit of the present invention.

The systems, devices, components, and methods disclosed in various publications may also be modified advantageously in accordance with the teachings set forth herein. Such publications include, but are not limited to, the following publications: (a) "The effects of age and cochlear hearing loss on temporal fine structure sensitivity, frequency selectivity, and speech reception in noise," Hopkins and Moore, J. Acoust. Soc. Am. 130 (1), 334-349 (2011); (b) "The effect of hearing loss on the resolution of partials and fundamental frequency discrimination," Moore and Glasberg, J. Acoust. Soc. Am. 130 (5), 2891-2901 (2011); (c) "Acoustic Coordinated Reset Neuromodulation in a Real Life Patient Population with Chronic Tonal Tinnitus," Hauptmann et al., BioMed Research International Article ID 569052, Hindawi Publishing Corporation (2015); (d) "Acoustic CR neuromodulation therapy for subjective tonal tinnitus: a review of clinical outcomes in an independent audiology practice setting," Williams et al., Front. Neurol. (2015); (e) "Validation of a Mobile Device for Acoustic Coordinated Reset Neuromodulation Tinnitus Therapy," Hauptmann et al., J. Am. Acad. Audio. 00:1-12 (2016), and (f) "optimal number of stimulation contacts for coordinated reset neuromodulation," Lysyansky et al., Frontiers in Neuroengineering, Vol. 6, pp 1-15 (2013).

According to some embodiments, there is provided a method of delivering an acoustic coordinated reset neuromodulation therapy to a patient comprising evaluating a tinnitus pitch of the patient using a pitch matching method to determine a tinnitus center frequency for the patient; determining, for the patient, respective center frequencies and intensities of first lower and first upper test tones located below and above the tinnitus center frequency, respectively; determining, for the patient, respective auditory filter bandwidths (AFBs) for the first lower and first upper test tones, each AFB having a respective width associated therewith; adjusting, for the patient, the center frequencies of the first lower and first upper test tones such that at least portions of the first lower and first upper test tones overlap with at least portions of the tinnitus auditory filter thereby to generate first lower and first upper therapeutic stimulation signals, and delivering to the patient the first lower and first upper therapeutic stimulation signals.

Such a method may further comprise any one or more of the first lower and first upper test tones having second and third center frequencies, respectively; determining, for the patient, respective center frequencies and intensities of second lower and second upper test tones located below and above the center frequencies of the first lower and first upper test tones, respectively; the second lower and second upper test tones having first and fourth center frequencies, respectively; determining, for the patient, respective AFBs for the second lower and second upper test tones, each AFB having a respective width associated therewith; adjusting, for the patient, the center frequencies of the second lower and second upper test tones such that at least portions of the second lower and second upper test tones overlap with at least portions of the first lower and first upper test tones thereby to generate second lower and second upper therapeutic stimulation signals; delivering to the patient the second lower and second upper therapeutic stimulation signals; and recording, patient feedback in response to changes in one or more of therapeutic signal intensities, therapeutic signal widths, and therapeutic signal center frequencies.

According to further embodiments, there is provided a system or device configured to deliver an acoustic coordinated reset neuromodulation therapy to a patient comprising means for evaluating a tinnitus pitch of the patient using a pitch matching method to determine a tinnitus center frequency for the patient; means for determining, for the patient, respective center frequencies and intensities of first lower and first upper test tones located below and above the tinnitus center frequency, respectively; means for determining, for the patient, respective auditory filter bandwidths (AFBs) for the first lower and first upper test tones, each AFB having a respective width associated therewith; means for adjusting, for the patient, the center frequencies of the first lower and first upper test tones such that at least portions of the first lower and first upper test tones overlap with at least portions of the tinnitus auditory filter thereby to generate first lower and first upper therapeutic stimulation signals, and means for delivering to the patient the first lower and first upper therapeutic stimulation signals.

Such systems or devices may further comprise any one or more of the first lower and first upper test tones having second and third center frequencies, respectively; means for determining, for the patient, respective center frequencies and intensities of second lower and second upper test tones located below and above the center frequencies of the first lower and first upper test tones, respectively; the second lower and second upper test tones having first and fourth center frequencies, respectively; means for determining, for the patient, respective AFBs for the second lower and second upper test tones, each AFB having a respective width associated therewith; means for adjusting, for the patient, the center frequencies of the second lower and second upper test tones such that at least portions of the second lower and second upper test tones overlap with at least portions of the first lower and first upper test tones thereby to generate second lower and second upper therapeutic stimulation signals; means for delivering to the patient the second lower and second upper therapeutic stimulation signals; and means for recording patient feedback in response to changes in one or more of therapeutic signal intensities, therapeutic signal widths, and therapeutic signal center frequencies.

The above-described embodiments should be considered as examples of the inventions described and disclosed herein, rather than as limiting the scope thereof. In addition to the foregoing embodiments, review of the detailed description and accompanying drawings will show that many other embodiments are contemplated that may not be explicitly disclosed or described herein. Accordingly, many combinations, permutations, variations and modifications of the foregoing embodiments will nevertheless fall within the spirit and scope of the various inventions described and disclosed herein. For example, implantable systems, devices and components may be adapted and configured for use in accordance with the teachings set forth herein, such as in cochlear implant devices and systems.

Although various methods and techniques have been described as being implemented in software, similar techniques can be implemented in hardware, firmware, or the like. Example hardware implementations include implementations within an application specific integrated circuit (ASIC), a field programmable gate array (FPGA), a programmable logic device, specifically designed hardware components, one or more processors, or any combination thereof. If implemented in software, a computer readable medium stores computer readable instructions, e.g., program code, that can be executed by a processor, DSP or other suitable computing device to carry out one of more of the techniques described above. For example, the computer readable medium can comprise random access memory (RAM), read-only memory (ROM), non-volatile random access memory (NVRAM), electrically erasable programmable read-only memory (EEPROM), flash memory, or the like. The computer readable medium can comprise computer readable instructions that when executed carry out one or more of the techniques described herein. The disclosed embodiments are presented for purposes of illustration and not limitation.

The invention claimed is:

1. A method of providing stimulation signals for acoustic coordinated reset neuromodulation therapy to be delivered to a patient, the method comprising:
providing an audio-detection threshold calibration, which defines a frequency dependent hearing level of the patient;
providing a frequency-discrimination threshold calibration, which defines an intensity dependent bandwidth of frequencies not discriminable by the patient;
evaluating a tinnitus frequency for tinnitus experienced by a patient;
determining a tinnitus bandwidth as the width of a tinnitus frequency band centered at the tinnitus frequency; and
generating at least one primary stimulation signal with a primary stimulation frequency and a primary stimulation intensity such that
the primary stimulation intensity exceeds a hearing level of the patient, as defined by the audio-detection threshold calibration at the primary stimulation frequency, by a predetermined quantity; and
the primary stimulation frequency is offset from the tinnitus frequency such that a primary stimulation frequency band and the tinnitus frequency band overlap by a predetermined amount, wherein the primary stimulation frequency band represents a frequency band centered at the primary stimulation frequency and having a primary stimulation bandwidth according to a bandwidth defined by the frequency-discrimination threshold calibration at the primary stimulation intensity.

2. The method according to claim 1, wherein generating the at least one primary stimulation signal comprises:
determining at least one initial primary stimulation frequency offset from the tinnitus frequency;
determining the primary stimulation intensity based on the at least one initial primary stimulation frequency according to the audio-detection threshold calibration;
determining the primary stimulation bandwidth as a bandwidth defined by the frequency-discrimination threshold calibration at the primary stimulation intensity;
modifying the at least one primary stimulation frequency so that the tinnitus frequency band and a modified primary stimulation frequency band overlap by the predetermined amount, wherein the modified primary stimulation frequency band represents a frequency band with the determined primary stimulation bandwidth centered at the modified primary stimulation frequency; and generating the at least one primary stimulation signal based on the modified primary stimulation frequency and the primary stimulation intensity.

3. The method according to claim 2, further comprising:

modifying the at least one primary stimulation intensity based on the modified at least one primary stimulation frequency such that the modified primary stimulation intensity exceeds a hearing level of the patient, as defined by the audio-detection threshold calibration at the modified primary stimulation frequency, by a predetermined quantity;

modifying the at least one primary stimulation bandwidth on the basis modified at least one primary stimulation intensity; and adjusting the at least one primary stimulation frequency so that the tinnitus frequency band and an adjusted primary stimulation frequency band overlap by the predetermined amount, wherein the adjusted primary stimulation frequency band represents a frequency band with the modified primary stimulation bandwidth centered at the adjusted primary stimulation frequency.

4. The method according to claim 1, wherein the at least one primary stimulation frequency comprises a first primary stimulation frequency and a second primary stimulation frequency, the first primary stimulation frequency having a positive offset from the tinnitus frequency and the second primary stimulation frequency having a negative offset from the tinnitus frequency.

5. The method according to claim 1, wherein determining the tinnitus bandwidth comprises:

calculating the tinnitus bandwidth as the tinnitus frequency multiplied by a predetermined factor.

6. The method according to claim 1, wherein determining the tinnitus bandwidth comprises:

determining a tinnitus intensity as an intensity of the tinnitus perceived by the patient; and determining the tinnitus bandwidth according to a bandwidth defined by the frequency-discrimination threshold calibration at the determined tinnitus intensity.

7. The method according to claim 1, further comprising testing the hearing level of the patient for a plurality of frequencies including the tinnitus frequency and the stimulation frequencies to obtain the audio-detection threshold calibration.

8. The method according to claim 1, further comprising:

estimating an ambient noise level parameter;

modifying the at least one primary stimulation intensity based on the ambient noise level parameter.

9. The method according to claim 1, further comprising:

generating at least one secondary stimulation signal with a secondary stimulation frequency and a secondary stimulation intensity such that the secondary stimulation intensity exceeds a hearing level of the patient, as defined by the audio-detection threshold calibration at the secondary stimulation frequency, by a predetermined quantity; and the secondary stimulation frequency is offset from the tinnitus frequency by an amount greater than the offset of the primary stimulation frequency such that a secondary stimulation frequency band and the tinnitus frequency band overlap by a predetermined amount, wherein the secondary stimulation frequency band represents a frequency band centered at the secondary stimulation frequency and having a secondary stimulation bandwidth according to a bandwidth defined by the frequency-discrimination threshold calibration at the secondary stimulation intensity.

10. The method according to claim 9, wherein generating the at least one secondary stimulation signal comprises:

determining at least one initial secondary stimulation frequency offset from the tinnitus frequency, wherein the offset of the at least one initial secondary stimulation frequency is greater than the offset of the at least one primary stimulation frequency;

determining the secondary stimulation intensity based on the at least one initial secondary stimulation frequency according to the audio-detection threshold calibration;

determining the secondary stimulation bandwidth as a bandwidth defined by the frequency-discrimination threshold calibration at the secondary stimulation intensity;

modifying the at least one secondary stimulation frequency so that the primary stimulation frequency band and a modified secondary stimulation frequency band overlap by the predetermined amount, wherein the modified secondary stimulation frequency band represents a frequency band with the determined secondary stimulation bandwidth centered at the modified secondary stimulation frequency; and generating the at least one secondary stimulation signal based on the modified secondary stimulation frequency and the secondary stimulation intensity.

11. The method according to claim 9, wherein the at least one secondary stimulation frequency comprises a first secondary stimulation frequency and a second secondary stimulation frequency, the first secondary stimulation frequency having a positive offset from the tinnitus frequency and the second secondary stimulation frequency having a negative offset from the tinnitus frequency.

12. The method according to claim 1, wherein the predetermined amount is in the range of about 2% to about 40% of the tinnitus frequency band, preferably in the range of about 5% to about 35% of the tinnitus frequency band, more preferably in a range of not more than about 30% of the tinnitus frequency band, most preferably in a range of not more than about 25% of the tinnitus frequency band.

13. A system or device configured to provide stimulation signals for acoustic coordinated reset neuromodulation therapy, the system comprising:

means for providing an audio-detection threshold calibration, which defines a frequency dependent hearing level of the patient;

means for providing a frequency-discrimination threshold calibration, which defines an intensity dependent bandwidth of frequencies not discriminable by the patient;

means for evaluating a tinnitus frequency for tinnitus experienced by a patient;

means for determining a tinnitus bandwidth as the width of a tinnitus frequency band centered at the tinnitus frequency; and means for generating at least one primary stimulation signal with a primary stimulation frequency and a primary stimulation intensity such that the primary stimulation intensity exceeds a hearing level of the patient, as defined by the audio-detection threshold calibration at the primary stimulation frequency, by a predetermined quantity; and the primary stimulation frequency is offset from the tinnitus frequency such that a primary stimulation frequency band and the tinnitus frequency band overlap by a predetermined amount, wherein the primary stimulation frequency band represents a frequency band centered at the primary stimulation frequency and having a primary stimulation bandwidth according to a bandwidth defined by the frequency-discrimination threshold calibration at the primary stimulation intensity.

14. A non-transitory computer readable medium having stored thereon computer readable code, which when loaded and executed by a computer system, causes the computer system to:

provide an audio-detection threshold calibration, which defines a frequency dependent hearing level of the patient;

provide a frequency-discrimination threshold calibration, which defines an intensity dependent bandwidth of frequencies not discriminable by the patient;

evaluate a tinnitus frequency for tinnitus experienced by a patient;

determine a tinnitus bandwidth as the width of a tinnitus frequency band centered at the tinnitus frequency; and generate at least one primary stimulation signal with a primary stimulation frequency and a primary stimulation intensity such that the primary stimulation intensity exceeds a hearing level of the patient, as defined by the audio-detection threshold calibration at the primary stimulation frequency, by a predetermined quantity; and the primary stimulation frequency is offset from the tinnitus frequency such that a primary stimulation frequency band and the tinnitus frequency band overlap by a predetermined amount, wherein the primary stimulation frequency band represents a frequency band centered at the primary stimulation frequency and having a primary stimulation bandwidth according to a bandwidth defined by the frequency-discrimination threshold calibration at the primary stimulation intensity.

15. The computer readable medium according to claim 14, wherein executing the code to cause the computer system to generate the at least one primary stimulation signal comprises:

determining at least one initial primary stimulation frequency offset from the tinnitus frequency;

determining the primary stimulation intensity based on the at least one initial primary stimulation frequency according to the audio-detection threshold calibration;

determining the primary stimulation bandwidth as a bandwidth defined by the frequency-discrimination threshold calibration at the primary stimulation intensity;

modifying the at least one primary stimulation frequency so that the tinnitus frequency band and a modified primary stimulation frequency band overlap by the predetermined amount, wherein the modified primary stimulation frequency band represents a frequency band with the determined primary stimulation bandwidth centered at the modified primary stimulation frequency; and generating the at least one primary stimulation signal based on the modified primary stimulation frequency and the primary stimulation intensity.

16. The computer readable medium according to claim 14, wherein the at least one primary stimulation frequency comprises a first primary stimulation frequency and a second primary stimulation frequency, the first primary stimulation frequency having a positive offset from the tinnitus frequency and the second primary stimulation frequency having a negative offset from the tinnitus frequency.

17. The computer readable medium according to claim 14, wherein the code that causes the computer system to determine the tinnitus bandwidth comprises code, which when loaded and executed by a computer system, causes the computer system to:

calculate the tinnitus bandwidth as the tinnitus frequency multiplied by a predetermined factor.

18. The computer readable medium according to claim 14, wherein the code that causes the computer system to determine the tinnitus bandwidth comprises code, which when loaded and executed by a computer system, causes the computer system to:

determine a tinnitus intensity as an intensity of the tinnitus perceived by the patient; and determine the tinnitus bandwidth according to a bandwidth defined by the frequency-discrimination threshold calibration at the determined tinnitus intensity.

19. The computer readable medium according to claim 14, further comprising code, which when loaded and executed by a computer system, causes the computer system to test the hearing level of the patient for a plurality of frequencies including the tinnitus frequency and the stimulation frequencies to obtain the audio-detection threshold calibration.

* * * * *